United States Patent
Wilson et al.

(10) Patent No.: US 7,578,015 B1
(45) Date of Patent: Aug. 25, 2009

(54) INFLATABLE NECK SUPPORT

(75) Inventors: Karen Wilson, Coral Springs, FL (US); Michael Anthony, Coral Springs, FL (US)

(73) Assignee: Karen L. Wilson, Coral Springs, FL (US)

( * ) Notice: Subject to any disclaimer, the term of this patent is extended or adjusted under 35 U.S.C. 154(b) by 0 days.

(21) Appl. No.: 12/331,493

(22) Filed: Dec. 10, 2008

(51) Int. Cl.
*A47G 9/10* (2006.01)

(52) U.S. Cl. .................................. 5/644; 5/636; 5/639

(58) Field of Classification Search .............. 5/644, 5/654, 655.3, 636, 639, 640, 645
See application file for complete search history.

(56) References Cited

U.S. PATENT DOCUMENTS

| | | | | |
|---|---|---|---|---|
| 655,087 | A * | 7/1900 | Jones | 5/644 |
| 2,700,779 | A * | 2/1955 | Tolkowsky | 5/632 |
| 2,880,428 | A * | 4/1959 | Forsland | 5/636 |
| 2,896,227 | A * | 7/1959 | Reed | 5/644 |
| 4,218,792 | A * | 8/1980 | Kogan | 5/636 |
| 4,494,261 | A * | 1/1985 | Morrow | 5/636 |
| 4,501,034 | A * | 2/1985 | Greenawalt | 5/644 |
| 4,660,238 | A | 4/1987 | Jay | |
| D295,936 | S * | 5/1988 | Sanders | D6/601 |
| 4,829,614 | A * | 5/1989 | Harper | 5/644 |
| 4,896,388 | A | 1/1990 | Bard | |
| 4,908,894 | A * | 3/1990 | Sanders | 5/640 |
| 4,918,774 | A * | 4/1990 | Popitz | 5/644 |
| D308,455 | S * | 6/1990 | Jenney | D6/601 |
| 5,016,303 | A * | 5/1991 | Tanaka et al. | 5/636 |
| 5,214,814 | A * | 6/1993 | Eremita et al. | 5/636 |
| 5,457,832 | A * | 10/1995 | Tatum | 5/636 |
| D383,026 | S | 9/1997 | Torbik | |
| 5,697,112 | A | 12/1997 | Colavito et al. | |
| 5,771,514 | A * | 6/1998 | Wilhoit | 5/644 |
| 5,809,597 | A * | 9/1998 | Shaw | 5/655.3 |
| 5,898,963 | A * | 5/1999 | Larson | 5/644 |
| 5,916,088 | A * | 6/1999 | Gueli | 5/639 |
| 5,948,013 | A | 9/1999 | Swezey et al. | |
| 6,047,425 | A * | 4/2000 | Khazaal | 5/644 |
| 6,131,219 | A * | 10/2000 | Roberts | 5/644 |
| 6,151,735 | A * | 11/2000 | Koby et al. | 5/644 |
| 6,237,598 | B1 | 5/2001 | Sereboff | |
| 6,317,908 | B1 * | 11/2001 | Walpin | 5/636 |
| 6,574,809 | B1 * | 6/2003 | Rathbun | 5/636 |
| 6,671,906 | B1 * | 1/2004 | Milligan | 5/636 |
| 6,817,049 | B1 * | 11/2004 | Hall | 5/636 |
| 6,981,288 | B1 * | 1/2006 | Hu | 5/636 |
| 6,993,800 | B2 * | 2/2006 | Greenawalt et al. | 5/636 |
| 7,316,041 | B2 * | 1/2008 | Guez | 5/636 |
| 7,516,504 | B2 * | 4/2009 | Guez | 5/636 |
| 2004/0006822 | A1 * | 1/2004 | Milligan | 5/636 |
| 2005/0257321 | A1 | 11/2005 | Kruger, Jr. | |
| 2006/0005314 | A1 * | 1/2006 | Lee | 5/644 |
| 2007/0095353 | A1 | 5/2007 | Ravikumar | |

* cited by examiner

*Primary Examiner*—Robert G Santos

(57) ABSTRACT

A neck supporting pillow apparatus that provides support for both the head and neck by way of adjustable inflation of the resting surface of the pillow is disclosed. An inflatable pillow structure has a head support section and a raised neck support section. The head support section includes a generally concave mid-portion bordered by generally planar side surfaces. The raised neck support includes a top surface that is generally convexly shaped to provide proper neck support. The pillow body defines an internal chamber with an openable cover to allow for insertion of a heat pack or cold pack. Independently inflatable firmness bladders allow for customization of support by increasing or decreasing the pressure in bladders.

4 Claims, 3 Drawing Sheets

INFLATABLE NECK SUPPORT

CROSS REFERENCE TO RELATED APPLICATIONS

N/A

STATEMENT REGARDING FEDERALLY SPONSORED RESEARCH OR DEVELOPMENT

N/A

COPYRIGHT NOTICE

A portion of the disclosure of this patent document contains material that is subject to copyright protection. The copyright owner has no objection to the facsimile reproduction by anyone of the patent document or patent disclosure as it appears in the Patent and Trademark Office patent file or records, but otherwise reserves all copyrights rights whatsoever.

BACKGROUND OF THE INVENTION

1. Field of the Invention

The present invention relates to an inflatable neck support apparatus, specifically a pillow device for maintaining proper head and neck positioning and support for sleeping or resting, which features adjustable level of air cushioning and adaptability for use with a heat or cold pack.

2. Description of Related Art

Ancestry of the pillow dates back to ancient Egypt. First used by the wealthy, traditional pillows were made from wood, stone or straw. As use became widespread, decorative aspects enhanced the popularity while feathers or down-fill created added comfort for sleeping or resting. Today, most pillows are filled with foam, synthetic fills, feathers, or down. Certain pillows are created with special shapes or fills in order to offer added support or alignment of the neck and/or spine. These specialty forms are often referred to as orthopedic or therapeutic support pillows. The emergence, popularity, and need for such devices results directly from an increase in head, neck and back strain in the human population.

Proper alignment of the skull and spine increases blood flow and eases tension throughout the body. The top seven vertebrae in the spine are classified as cervical vertebrae, which connect the skull to the lower portion of the spine. When not properly aligned, pain and tension, sometimes resulting in muscles spasm or pinched nerves, may result. While cartilage between each vertebrae provides a natural cushion, proper positioning of the cervical vertebrae in line with the head and shoulders during sleeping provides relief to the joints. Anatomically, the optimal position for the cervical vertebrae is referred to as the neutral position. Such position is achieved whilst standing upright with proper posture. As this posture is difficult to achieve in a reclined stance, proper neck support during rest is difficult to achieve.

Current art includes a variety of specialty pillows, many of which claim to properly support a particular body part. Many of these designs have focused on the head, neck and shoulders. Created from materials such as polyester foam or fiber, improvements are now constructed of viscoelastic memory foam made of polyurethane, which adds heat sensitive properties while contouring to and holding the shape of the body. These types of products may be helpful, but have a preformed curve as part of the design. This element of the design limits the adjustability of the curved support of the neck. As all human bodies are somewhat unique, the amount of support required varies from person to person. When using pillows such as feather or buckwheat, the contents can shift during use, thereby affecting the proper support of the head and/or neck. As a result of limitations in the prior art, there exists a need for improvements in current therapeutic pillows to assist in proper alignment of the neck whilst in a reclining position.

BRIEF SUMMARY OF THE INVENTION

The present invention overcomes the limitations and disadvantages present in the art by providing an improved pillow apparatus to provide support for the neck by way of adjustable inflation of the resting surface of the pillow. The inflatable portion will be airtight such that support will not be compromised by unintentional deflation. Further, the present embodiment provides a method for insertion of a heat or cold pack, thereby allowing the consumer to modify the therapeutic effects as required. In a preferred embodiment, the present invention includes an inflatable structure having a head support section and a raised neck support section. In an alternate embodiment, the base could be constructed of any other formable surface, which holds its shape with sufficient strength to support the weight of a human head. Contemplation of alternate embodiments includes any valve-type inflation method, such as manual, foot pump, or pressurized air insertion. The head support section includes a generally concave mid-portion bordered by generally planar side surfaces. The raised neck support includes a top surface that is generally convexly shaped to provide proper neck support. The pillow body defines an internal chamber with an openable cover to allow for insertion of a heat pack or cold pack.

Accordingly, it is an object of the present invention to provide improvements in therapeutic neck support.

Another object of the present invention is to provide an inflatable pillow device for use in adjustable neck support.

Another object of the present invention is to provide such an apparatus adapted with a fill valve system for intake and release of air pressure of the pillow.

Yet another object of the present invention is to provide such an apparatus adapted for ease of movement and travel, where the device is lightweight and portable.

Still another object of the present invention is to provide such an apparatus adapted with a hollow internal area for insertion of a heat pack or cold pack for use in conjunction with variable air pressurized pillow support.

These and other objects are met by the present invention which will become more apparent from the accompanying drawings and the following detailed description of the drawings and preferred embodiments.

BRIEF DESCRIPTION OF THE SEVERAL VIEWS OF THE DRAWINGS

FIG. 3 is a rear top perspective view thereof;

DETAILED DESCRIPTION OF TH INVENTION

Figure 1:
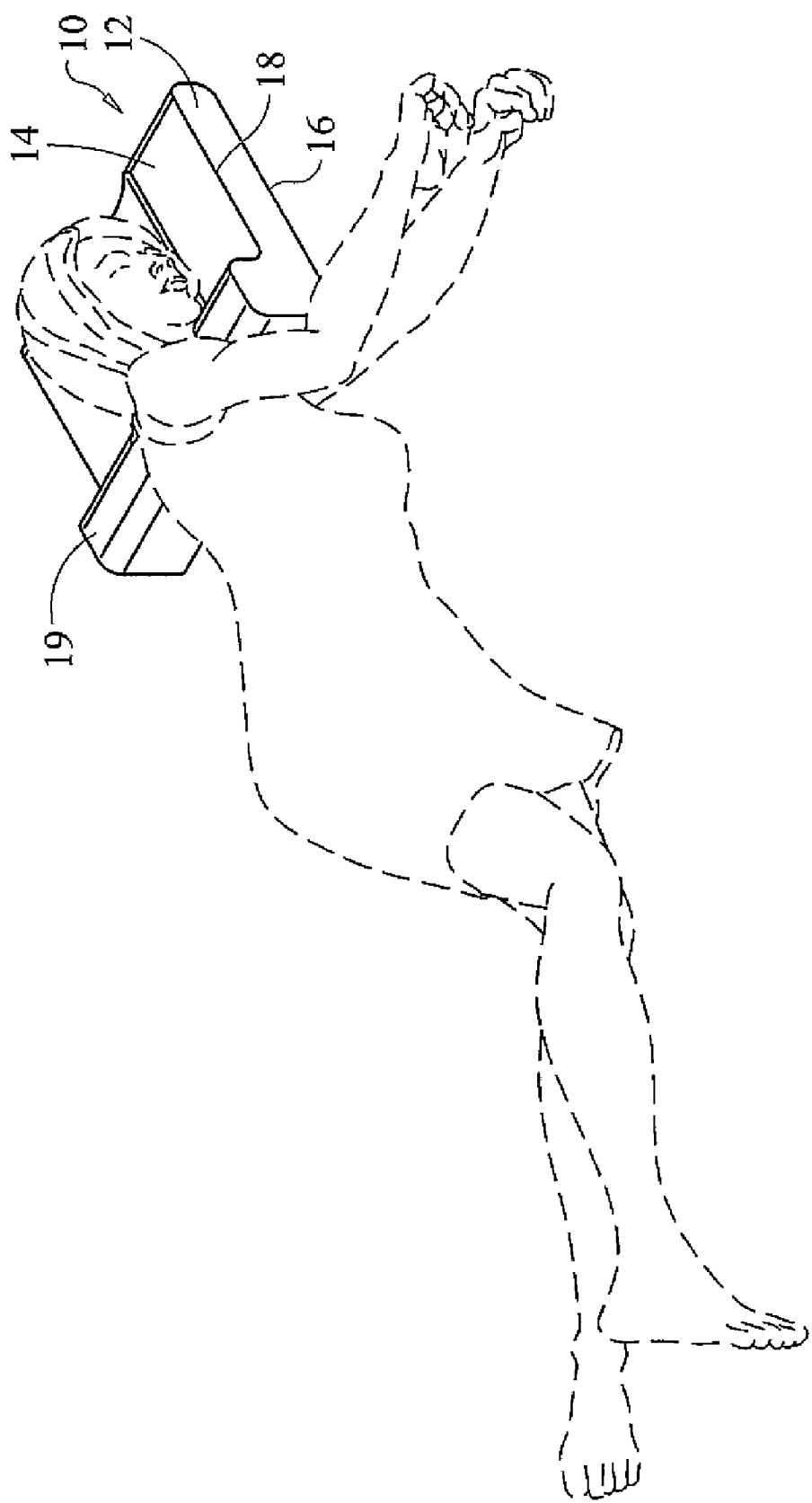
FIG. 1 is a front top perspective view of an inflatable neck support in accordance with the present invention in relation to a user.

With reference now to the drawings, FIGS. 1-5 depict an inflatable neck support apparatus, generally referenced as 10, specifically adapted for supporting the neck of the user in accordance with the present invention. Neck support apparatus 10, preferably comprises an inflatable body 12 having a top 14 and a bottom 16. Inflatable body 12 is preferably fabricated from a flexible material that is impervious to air (e.g air tight), such as plastic, latex, nylon, etc. Inflation and deflation is facilitated by a fill port 13. Fill port 13 may comprise any suitable air valve structure. In a preferred embodiment, top 14 defines a head support section 18 and a raised neck support section 19. As noted above, the main body is inflatable, however, the top surface may include a resilient surface for increased comfort.

Figure 2:
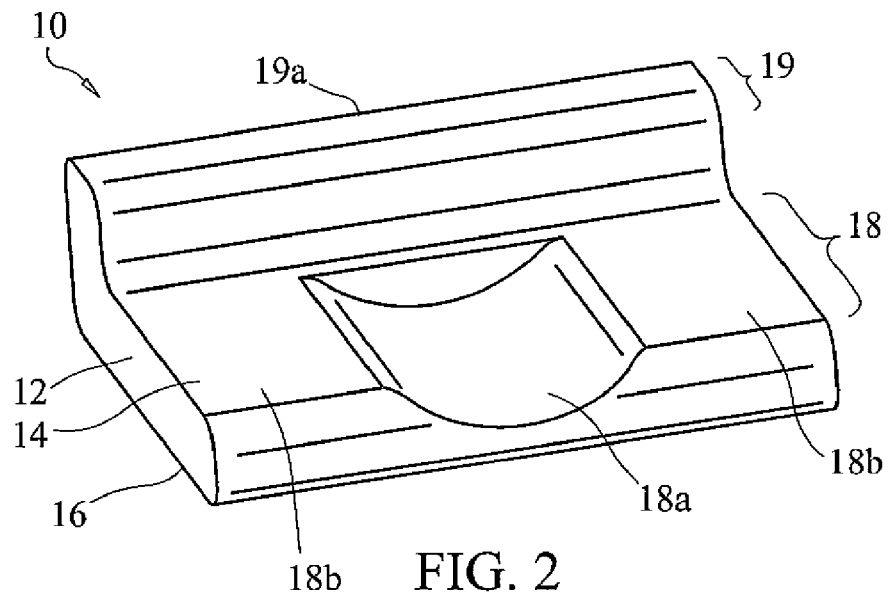
FIGS. 2 and 3 are rear perspective views thereof.
Figure 3:
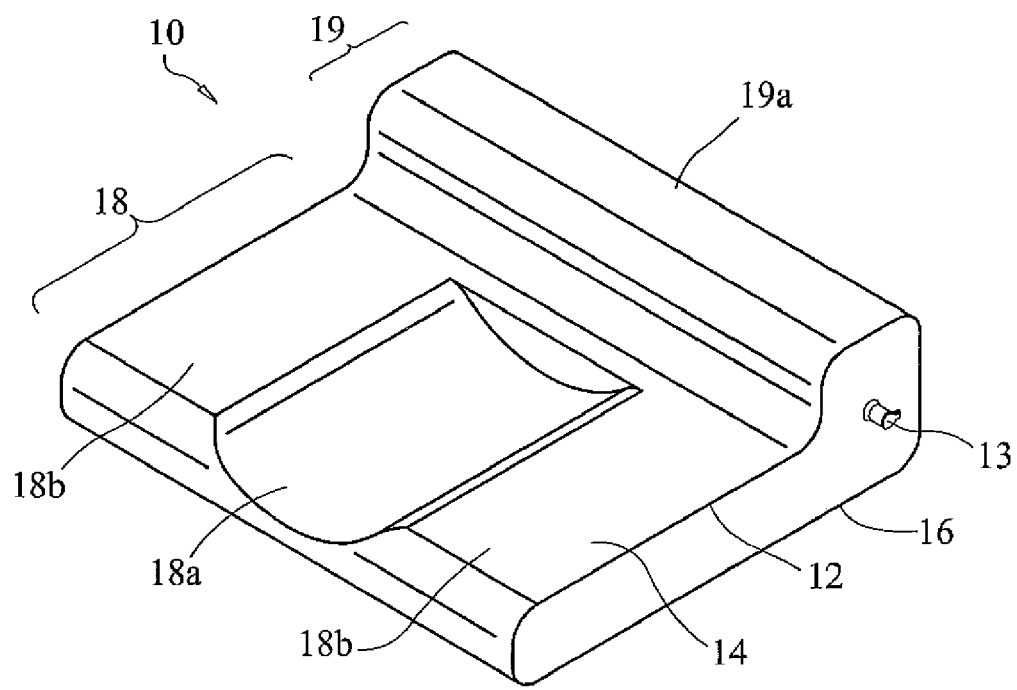

Head support section 18 includes a generally concave mid-portion 18a, bordered by generally planar side surfaces, referenced as 18b. The raised neck support includes a top surface 19A that is generally convexly shaped to provide proper neck support. More particularly head support section 18 of neck support pillow 10 includes a mid-portion 18a that forms a generally shallow concave shape as it extends from the left to the right side as best illustrated in FIGS. 2 and 3. Providing mid-portion 18a with a generally concave shape provides a surface for receiving and cradling the user's head. Mid-portion 18a is juxtaposed between left and right generally planar side portions, each referenced as 18b. Planar side portions 18b provide the user with alternately shaped and positioned surfaces upon which to place his/her head whilst lying on their back or either side. Planar side portions 18b are also slightly elevated relative to concave mid-portion 18a so as to offer the user a resting position wherein the height differential relative to the raised neck support section 19 is reduced. As noted above, neck support section 19 includes a generally convexly shaped surface (relative to the user's spine) 19a for supporting the user's neck. Surface 19a is elevated relative to head support section 18 so as to conform to the shape of the user's body, namely to provide a structure that engages and supports the user's neck while the user's head is supported by head support section 18. In a preferred embodiment, the neck support section 19 is elevated approximately 2.0"-4.0" above the planer surface (e.g. mattress) on which the device is resting.

Figure 4:
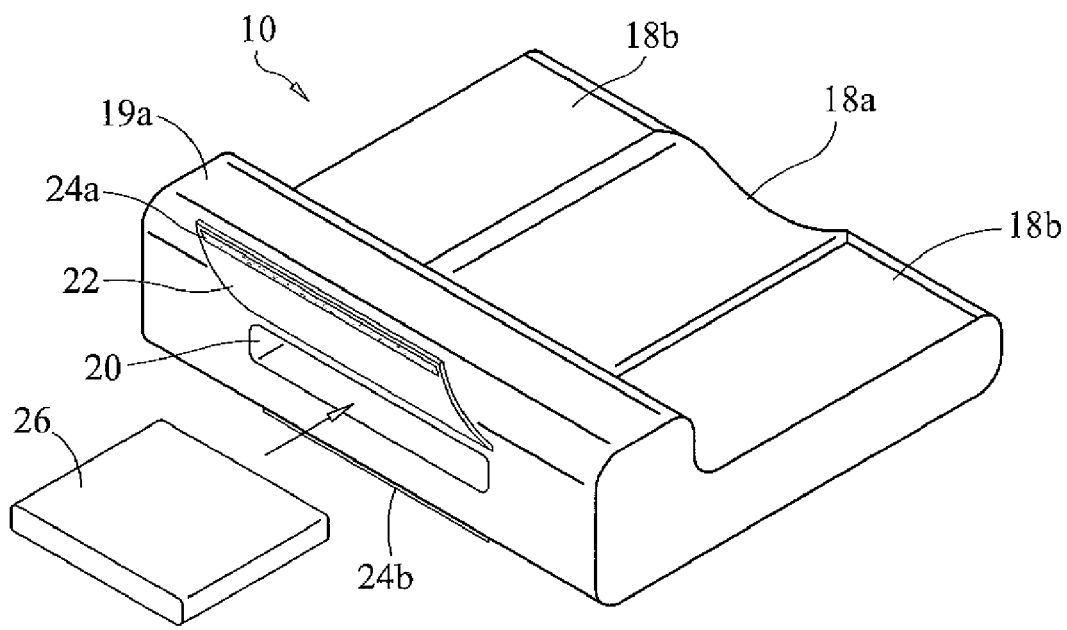
FIG. 4 is a front perspective view thereof.

Neck support pillow 10 is adapted such that main body 12 defines an internal chamber, referenced as 20, having an access opening defined on the front side thereof as best illustrated in FIG. 4. A flap 22 is configurable from a closed configuration wherein flap 22 is disposed in substantial covering relation with the opening to internal chamber 20, to an open configuration to allow for access to internal chamber 20 as best illustrated in FIG. 4. Flap 22 and body 12 preferably include hook and loop fastening material, referenced as 24a and 24b to allow for flap 20 to be removably secured in the closed configuration. Chamber 20 is intended to conceal a thermal pack, referenced as 26, such as a hot pack or cold pack, or may be used with the cavity being empty. More particularly, chamber 20 provides an internal compartment capable of receiving a thermal pack for the purpose of heating or cooling top surface 19a thereby providing the user with the therapeutic benefits of heat or cold applied to the neck. As should be apparent, flap 22 functions to maintain the heat pack or cold pack within chamber 20 when in the closed configuration by engagement of hook and loop fastening material 24a and 24b.

Figure 5:
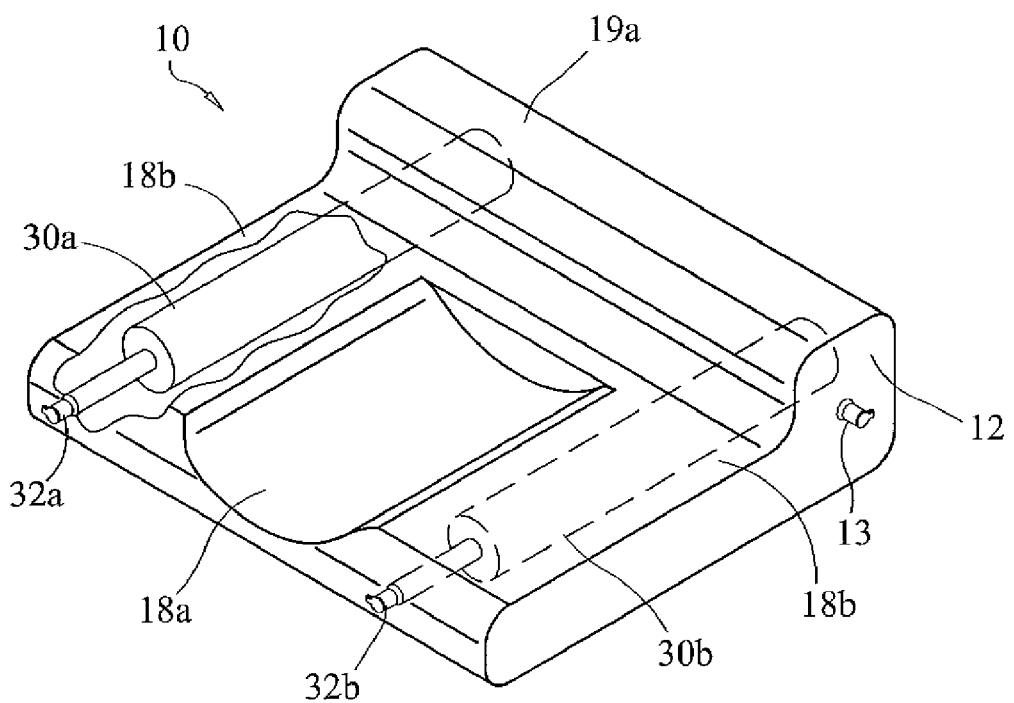
FIG. 5 is a rear perspective view thereof with partial cutaway illustrating adjustable firmness inflation bladders.

FIG. 5 is a perspective view with partial cutaway to reveal independently inflatable left and right internal firmness bladders, referenced as 30a and 30b. Each firmness bladder 30 includes an inflation valve, referenced as 32a and 32b, respectively. A significant aspect of the present invention involves providing firmness bladders 30 that allow the user to independently adjust the firmness provided by supporting surfaces 18b. Firmness bladders 30 thus allow for customization of support, a feature considered significant as the degree and extent of neck pain differs in afflicted persons, by selectively increasing or decreasing pressure in bladders 30.

The instant invention has been shown and described herein in what is considered to be the most practical and preferred embodiment. It is recognized, however, that departures may be made therefrom within the scope of the invention and that obvious modifications will occur to a person skilled in the art.

What is claimed is:

1. A neck support pillow for use by a person while lying on his/her back or either side, said neck support pillow comprising:
    an inflatable body fabricated from air impermeable material, and generally sized and shaped for positioning in supporting relation beneath the neck of a person when the person is lying down;
    said body including a top, a bottom, a length and a width;
    said top generally including a head supporting surface and a neck supporting surface, said neck supporting surface elevated with respect to said head supporting surface, being generally convexly shaped and having a length substantially equal and parallel to said length of said body;
    said head supporting surface including a generally concave mid-portion having a substantially uniform cross-section and generally planar side surfaces disposed on either side of said mid-portion, wherein said mid-portion and said side surfaces each have a length extending substantially parallel to said width of said body; said body defining an opening leading to a chamber disposed internal to said body between said top and bottom, said chamber for receiving a thermal therapy pack removably inserted therein; and
    means for inflating said body.

2. A neck support pillow according to claim 1, wherein said bottom is generally planar.

3. A neck support pillow according to claim 1, further including first and second independently inflatable firmness bladders contained within said inflatable body.

4. A neck support pillow according to claim 3, wherein said first and second independently inflatable firmness bladders are disposed below said generally planar side surfaces.

* * * * *